US012686050B2

(12) United States Patent
Islam et al.

(10) Patent No.: US 12,686,050 B2
(45) Date of Patent: Jul. 21, 2026

(54) PASSIVATED SILVER NANOPARTICLE COATINGS AND METHODS OF MAKING THE SAME

(71) Applicants: Arizona Board of Regents on behalf of Arizona State University, Scottsdale, AZ (US); CACTUS MATERIALS, INC., Scottsdale, AZ (US)

(72) Inventors: Rafiqul Islam, Gilbert, AZ (US); Francois Perreault, Tempe, AZ (US)

(73) Assignees: Arizona Board of Regents on behalf of Arizona State University, Scottsdale, AZ (US); CACTUS MATERIALS, INC., Tempe, AZ (US)

( * ) Notice: Subject to any disclaimer, the term of this patent is extended or adjusted under 35 U.S.C. 154(b) by 797 days.

(21) Appl. No.: 18/000,587

(22) PCT Filed: Jun. 2, 2021

(86) PCT No.: PCT/US2021/035410
§ 371 (c)(1),
(2) Date: Dec. 2, 2022

(87) PCT Pub. No.: WO2021/247676
PCT Pub. Date: Dec. 9, 2021

(65) Prior Publication Data
US 2023/0211408 A1 Jul. 6, 2023

Related U.S. Application Data

(60) Provisional application No. 63/035,355, filed on Jun. 5, 2020.

(51) Int. Cl.
*B22F 1/00* (2022.01)
*A01N 25/26* (2006.01)
(Continued)

(52) U.S. Cl.
CPC .............. *B22F 1/054* (2022.01); *A01N 25/26* (2013.01); *A01N 59/16* (2013.01); *A01P 1/00* (2021.08);
(Continued)

(58) Field of Classification Search
CPC .. B22F 1/054; B22F 1/145; B22F 1/16; B22F 1/056; B22F 1/142; B22F 9/24;
(Continued)

(56) References Cited

U.S. PATENT DOCUMENTS

2006/0115536 A1* 6/2006 Yacaman .............. B22F 1/0547
424/618
2015/0147372 A1 5/2015 Agrawal
(Continued)

OTHER PUBLICATIONS

Proposal Summary, as supplied by applicants (Year: 2019).*
(Continued)

*Primary Examiner* — James E Mcdonough
(74) *Attorney, Agent, or Firm* — Riverside Law LLP

(57) ABSTRACT

The instant disclosure is directed to passivated silver nanoparticle coatings and methods of making the same. A method may comprise obtaining a substrate having a surface, exposing the surface to a plurality of silver nanoparticles, applying a nucleating agent to the silver nanoparticles to form a plurality of silver cores, and passivating the silver cores by applying a sulfidation agent to the silver cores to form silver sulfide shells around the silver cores, thereby forming a coating comprising a plurality of sulfidated silver nanoparticles having a core-shell structure. The method may be used to form a coating comprising a plurality of sulfidated silver nanoparticles having a core-shell structure.

20 Claims, 16 Drawing Sheets

(51) Int. Cl.

| | |
|---|---|
| *A01N 59/16* | (2006.01) |
| *A01P 1/00* | (2006.01) |
| *B01D 61/08* | (2006.01) |
| *B01D 61/18* | (2006.01) |
| *B01D 67/00* | (2006.01) |
| *B01D 69/12* | (2006.01) |
| *B01D 71/02* | (2006.01) |
| *B22F 1/054* | (2022.01) |
| *B22F 1/142* | (2022.01) |
| *B22F 1/145* | (2022.01) |
| *B22F 1/16* | (2022.01) |
| *B22F 9/24* | (2006.01) |
| *B82Y 5/00* | (2011.01) |
| *B82Y 40/00* | (2011.01) |
| *C09D 1/00* | (2006.01) |
| *C09D 5/16* | (2006.01) |
| *C23C 24/00* | (2006.01) |

(52) U.S. Cl.

CPC ............. *B01D 61/08* (2013.01); *B01D 61/18* (2013.01); *B01D 67/00933* (2022.08); *B01D 69/1214* (2022.08); *B01D 71/022* (2013.01); *B22F 1/056* (2022.01); *B22F 1/142* (2022.01); *B22F 1/145* (2022.01); *B22F 1/16* (2022.01); *B22F 9/24* (2013.01); *B82Y 5/00* (2013.01); *B82Y 40/00* (2013.01); *C09D 1/00* (2013.01); *C09D 5/1618* (2013.01); *C23C 24/00* (2013.01); *B01D 2323/21811* (2022.08); *B01D 2325/48* (2013.01); *B22F 2301/255* (2013.01); *B22F 2302/45* (2013.01); *B22F 2304/054* (2013.01); *B22F 2304/058* (2013.01); *B22F 2998/10* (2013.01); *B22F 2999/00* (2013.01)

(58) Field of Classification Search

CPC . A01P 1/00; B01D 67/00933; B01D 69/1214; B01D 61/08; B01D 61/18; B01D 71/022; A01N 25/26; A01N 59/16; B82Y 5/00; B82Y 40/00; C09D 1/00; C09D 5/1618; C23C 24/00

USPC ......................................................... 106/1.19

See application file for complete search history.

(56) References Cited

U.S. PATENT DOCUMENTS

| | | | |
|---|---|---|---|
| 2015/0374878 A1 | 12/2015 | Carter | |
| 2024/0325988 A1* | 10/2024 | Baig | B01D 69/1071 |
| 2026/0008016 A1* | 1/2026 | Baig | B01D 69/1071 |

OTHER PUBLICATIONS

"Controlling Silver Release from Antimicrobial Surface Coatings for Biofouling Control", Proposal Summary. Small Business Technology Transfer (STTR) Program, US, vol. 19-1-T6.06-4319, pp. 1-2, Proposal Summary. Small Business Technology Transfer (STTR) Program, URL: https://sbir.nasa.gov/SBIR/abstracts/19/sttr/phase1/STTR-19-1-T6.06-4319.html, (Aug. 5, 2021), XP009534068.

Anonymous, "NASA SBIR/STTR Interactive Participation Guide; Small Business Innovation Research Small Business Technology Transfer ", (Oct. 19, 2021), URL: https://sbir.nasa.gov/content/nasa-sbirsttr-interactive-participation-guide, XP055895728.

Anonymous, "National Aeronautics and Space Administration Small Business Innovation Research (SBIR) & Small Business Technology Transfer (STTR) Fiscal Year 2019 General Solicitation", (Mar. 29, 2019), URL: https://sbir.nasa.gov/solicit-detail/61545, XP055895730.

Mohammed Rafiqul Islam, "Controlling Silver Release from Antimicrobial Surface Coatings for Biofouling Control", US, vol. 19-1-T6.06-4319, pp. 1-2, NASA STTR 2019-Solicitation T6.06-4319: Spacecraft Water Sustainability through Nanotechnology, URL: https://sbir.nasa.gov/SBIR/abstracts/19/sttr/phase1/STTR-19-1-T6.06-4319.html, (Aug. 5, 2021), XP009534068.

Ranjbari, K., Lee, W. L., Ansari, A., Barrios, A. C., Sharif, F., Islam, R., & Perreault, F. (2022). Controlling silver release from antibacterial surface coatings on stainless steel for biofouling control. Colloids and Surfaces B: Biointerfaces, 216, 112562.

* cited by examiner

3mM 300 mM

PASSIVATED SILVER NANOPARTICLE COATINGS AND METHODS OF MAKING THE SAME

CROSS-REFERENCE TO RELATED APPLICATIONS

The present application is a U.S. national phase application filed under 35 U.S.C. § 371 claiming benefit to PCT International Patent Application No. PCT/US21/35410, filed on Jun. 2, 2021, which claims priority to and benefit of U.S. Provisional Application No. 63/035,355, filed Jun. 5, 2020, each of which are incorporated herein by reference in their entireties.

GOVERNMENT INTERESTS

This invention was made with government support under 1449500 awarded by the National Science Foundation and 80NSSC19C0566 awarded by the National Aeronautical & Space Administration. The government has certain rights in the invention.

TECHNICAL FIELD

The present disclosure relates generally to silver coatings and methods of making and using such coatings. The silver coatings described herein may be used in a variety of applications, including water treatment, medical supplies, medical devices, textiles, and surfaces for which biocidal properties and biofouling control are important.

BACKGROUND

Silver is used as a biocide for disinfection and biofouling control in a variety of applications, including water treatment, medical supplies, medical devices, textiles, and the like. However, antimicrobial coatings containing silver nanoparticles have high leaching rates, leading to only short-term effectiveness, which increases both overall cost and the risk of biofilm development. Therefore, there exists a need for a silver coating that demonstrates both a low silver leaching rate and sustained biocidal properties.

SUMMARY

The instant disclosure is directed to passivated silver nanoparticle coatings and methods of making the same. In an embodiment, a method may comprise obtaining a substrate having a surface, and exposing the surface to a plurality of silver nanoparticles (Ag NPs). The method may further comprise applying a nucleating agent to the silver nanoparticles to form a plurality of silver cores. The method may still further comprise passivating the silver cores by applying a sulfidation agent to the silver cores to form silver sulfide ($Ag_2S$) shells around the silver cores, thereby forming a coating comprising a plurality of sulfidated silver nanoparticles ($Ag/Ag_2S$) having a core-shell structure. In some embodiments, the plurality of sulfidated silver nanoparticles may be uniformly distributed on the surface. In certain embodiments, the silver cores may have a diameter from about 10 nm to about 100 nm.

In certain embodiments, the substrate may be selected from the group consisting of a water treatment instrument, a surgical instrument, an implantable medical device, a catheter, a bandage, a furniture article, a garment, and combinations thereof. In some embodiments, the substrate may comprise a material selected from the group consisting of a metal, a metal alloy, a polymer, a membrane, a textile, and combinations thereof. In an embodiment, the substrate may comprise stainless steel.

In some embodiments, the nucleating agent may be selected from the group consisting of sodium borohydride, hydrazine, D-glucose, hyaluronic acid, and combinations thereof. In an embodiment, the nucleating agent may be D-glucose. In certain embodiments, the nucleating agent may have a concentration from about 3 mM to about 300 mM.

In certain embodiments, the sulfidation agent may be selected from the group consisting of sodium sulfide, sodium thiosulfate, thiocarbamide, thioacetamide, and combinations thereof. In an embodiment, the sulfidation agent may comprise sodium sulfide. In some embodiments, the sulfidation agent may have a concentration from about $10^{-1}$ M to about $10^{-5}$ M. In certain embodiments, the sulfidation agent may be applied to the sliver cores for a time period of from about 1 hour to about 12 hours.

In some embodiments, a coating may be formed by the method described above. In certain embodiments, the resulting composition may comprise a plurality of sulfidated silver nanoparticles having a core-shell structure. In some embodiments, a substrate as described above may have a surface coated with the resulting composition.

3

Figures 9A, 9B:
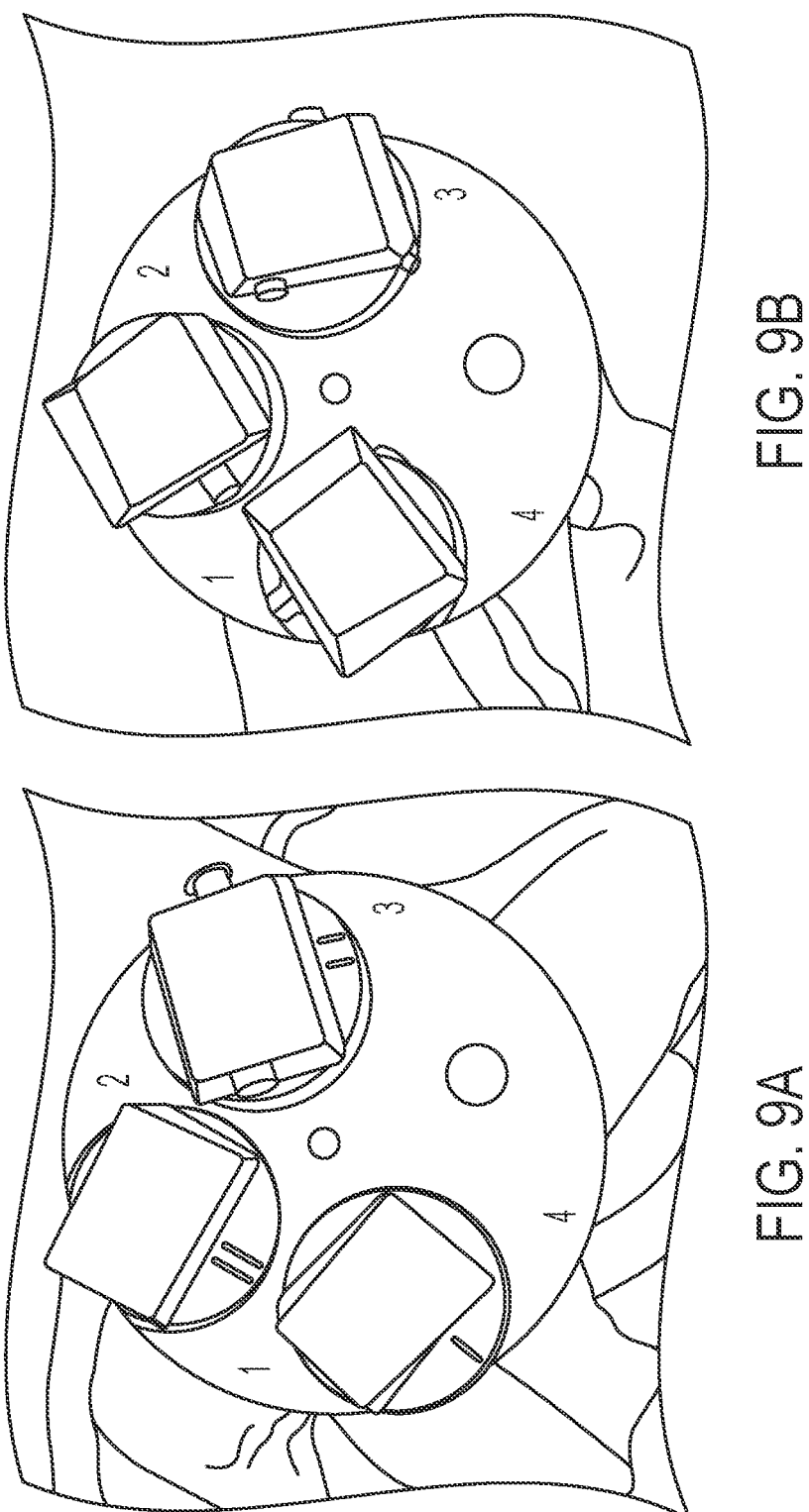
FIG. 9A shows a surface exposed to a composition using D-glucose as a nucleation agent, as described herein.

FIG. 9B show a surface exposed to a composition using sodium borohydride (NaHB$_4$) as a nucleation agent, as described herein.

Figures 10A, 10B:
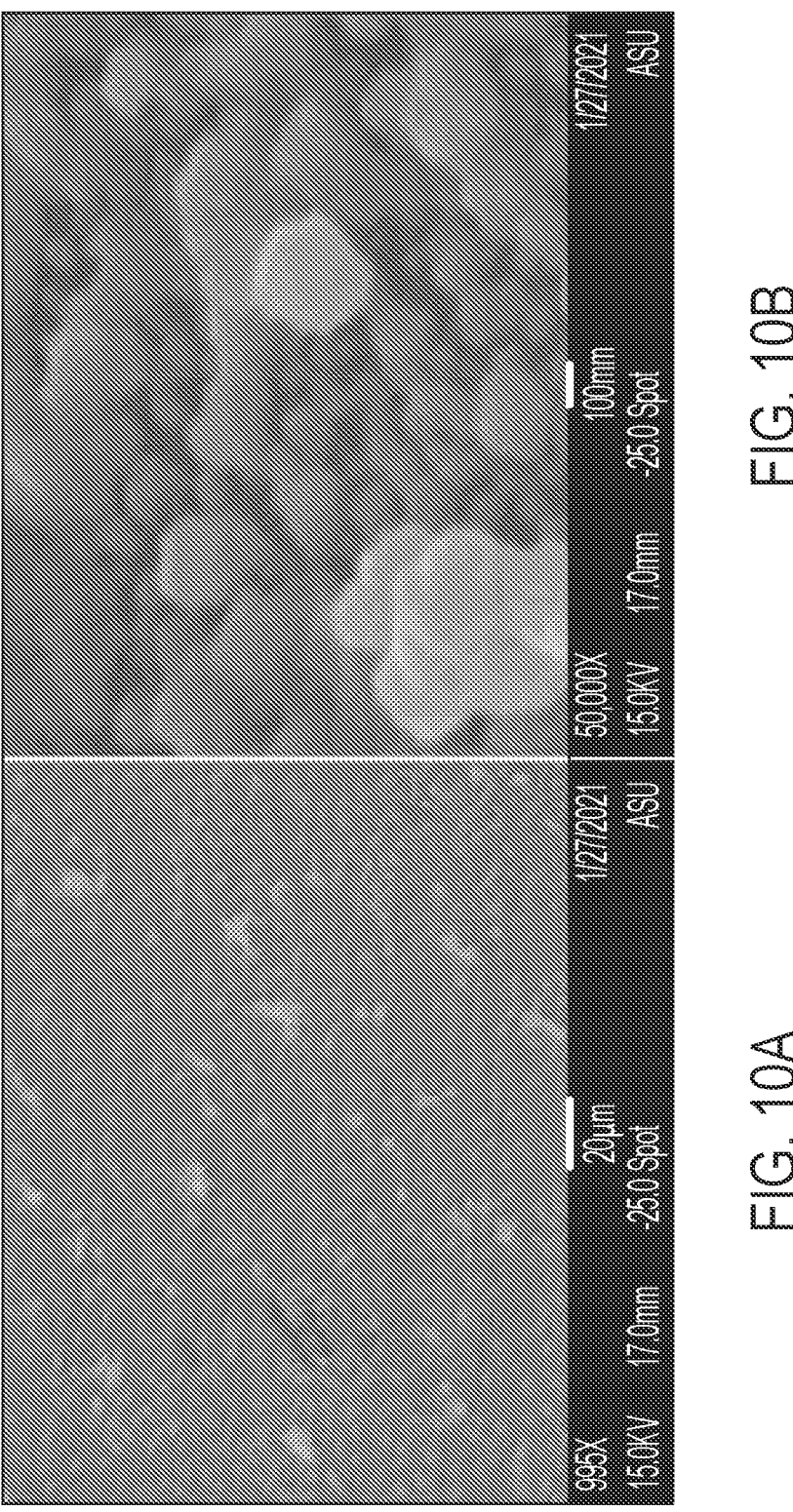

FIG. 10A shows an SEM image of Ag NPs exposed to D-glucose as a nucleation agent, as described herein.

FIG. 10B shows a higher-magnification SEM image of Ag NPs exposed to D-glucose as a nucleation agent, as described herein.

Figure 10C:
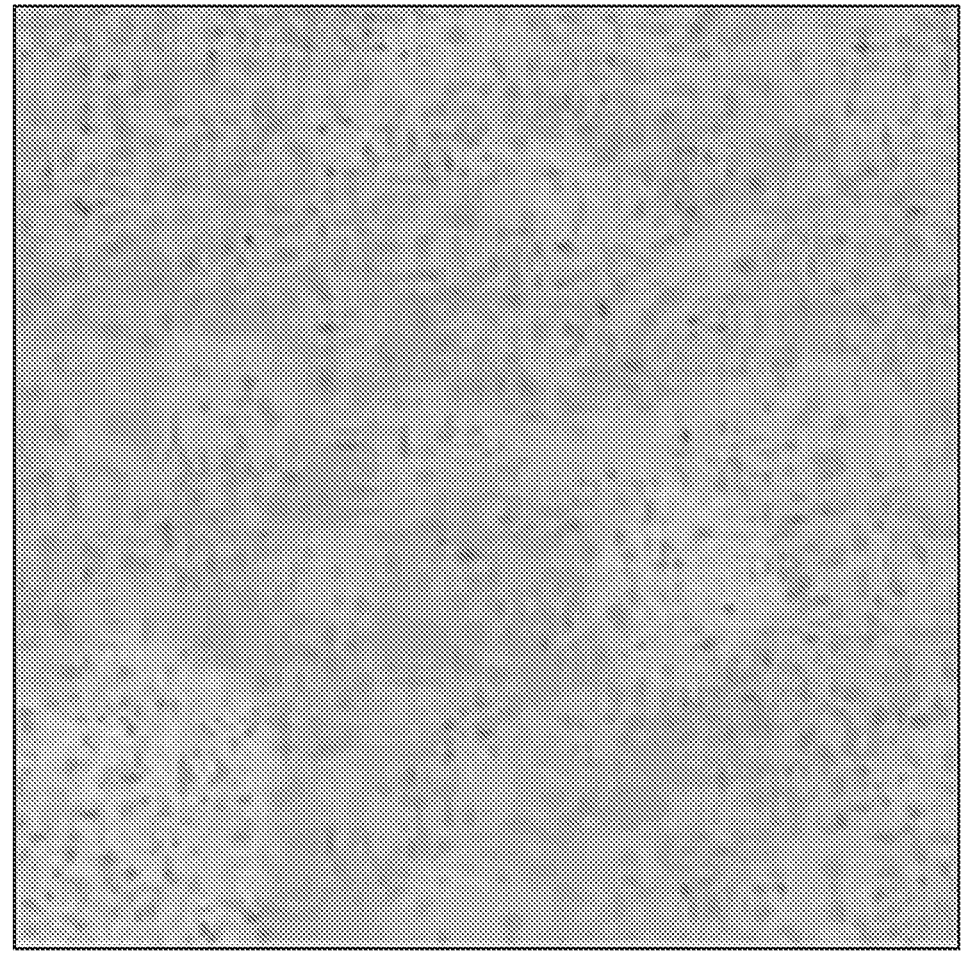

FIG. 10C shows an SEM image of Ag NPs exposed to D-glucose as a nucleation agent, as described herein.

DETAILED DESCRIPTION

This disclosure is not limited to the particular systems, devices and methods described, as these may vary. The terminology used in the description is for the purpose of describing the particular versions or embodiments only, and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" include plural references, unless the context clearly dictates otherwise. Thus, for example, reference to a "nanoparticle" is a reference to one or more nanoparticles and equivalents thereof known to those skilled in the art, and so forth.

As used herein, the term "about" means plus or minus 10% of the numerical value of the number with which it is being used. Therefore, about 50 mm means in the range of 45 mm to 55 mm.

As used herein, the term "consists of" or "consisting of" means that the device or method includes only the elements, steps, or ingredients specifically recited in the particular claimed embodiment or claim.

In embodiments or claims where the term "comprising" is used as the transition phrase, such embodiments can also be envisioned with replacement of the term "comprising" with the terms "consisting of" or "consisting essentially of."

As used herein, the terms "passivate" and "passivated" refer substances having reduced reactivity. A passivated surface, for example, is one that has been made less reactive, or in some circumstances unreactive, by altering the surface layer. In some examples, a surface may be passivated by exposing at least a portion of it to a sulfidation agent.

As used herein, the phrase "level of sulfidation" refers to a ratio of silver to sulfide (i.e., an Ag:S ratio). In other words, the level or degree of sulfidation of the compositions described herein are expressed as Ag:S ratios.

As will be understood by one skilled in the art, for any and all purposes, such as in terms of providing a written description, all ranges disclosed herein are intended as encompassing each intervening value between the upper and lower limit of that range and any other stated or intervening value in that stated range. All ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 particles refers to groups having 1, 2, or 3 particles as well as the range of values greater than or equal to 1 particle and less than or equal to 3 particles. Similarly, a group having 1-5 cells refers to groups having 1, 2, 3, 4, or 5 particles, as well as the range of values greater than or equal to 1 particle and less than or equal to 5 particles, and so forth.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

All percentages, parts and ratios are based upon the total weight of the compositions and all measurements made are at about 25° C., unless otherwise specified.

Silver is used as a biocide for disinfection and biofouling control in a variety of applications, including water treatment, medical supplies, medical devices, textiles, and the like. However, antimicrobial coatings containing silver nanoparticles have high leaching rates, leading to only short-term effectiveness, which increases both overall cost and the risk of biofilm development. Therefore, there exists a need for a silver coating that demonstrates both a low silver leaching rate and sustained biocidal properties.

The coatings and methods described herein are able to extend the lifetime of silver nanoparticle-based antimicrobial coatings without affecting their anti-biofouling performance. The methods described herein employ partial sulfidation to passivate silver nanoparticles, forming Ag/Ag$_2$S core-shell structures having low silver leaching rates but excellent long-term biocidal properties. Optimal physico-chemical properties that balance the dissolution rate and biocidal activity in the passivated silver nanoparticle coatings described herein are employed.

In particular, the coatings and methods described herein aim to improve the long-term performance of silver-based surface coatings used for biofouling control. The methods described herein employ several steps, including but not limited to the generation of nanoscale silver particles (Ag NPs) on a surface, which provides a high surface area for biocidal action, and the passivation of Ag NPs by the formation of a silver sulfide ($Ag_2S$) shell for slower silver release. The resulting $Ag/Ag_2S$ core-shell structure appears to extend the lifetime of antimicrobial coatings and increase their overall biofouling control performance over time. The passivation of Ag NPs to $Ag/Ag_2S$ core-shell structures is believed to slow the release of ionic silver to extend the lifetime of silver-based surface coatings, thereby improving the overall performance of the coatings for biofouling control over time.

Figure 1:
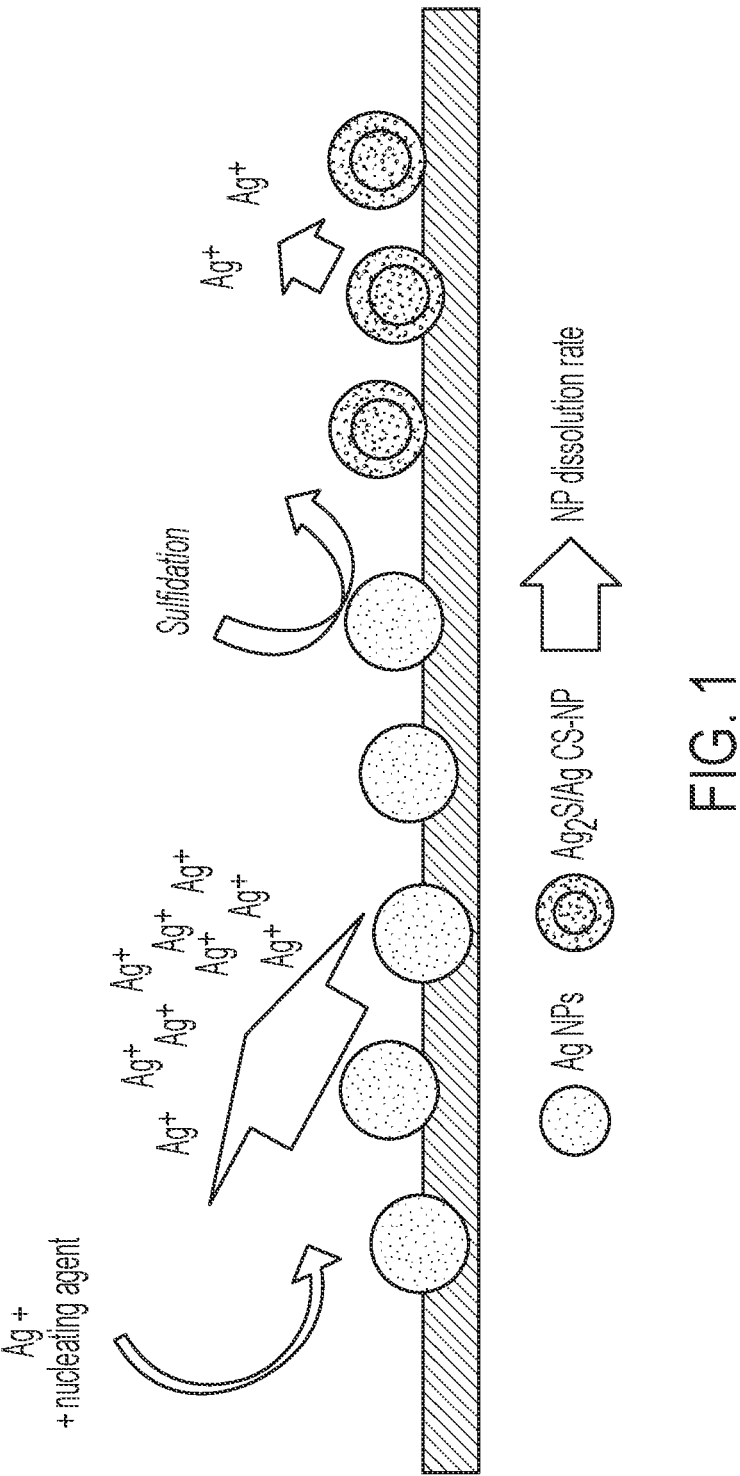
FIG. 1 is a schematic representation of an embodiment of a method described herein.

The methods described herein involve careful control of the silver passivation stage, which results in an $Ag/Ag_2S$ core-shell structure that retains good antimicrobial properties despite its reduced solubility. FIG. 1 is a schematic representation of an embodiment of the methods described herein: silver nanoparticles (Ag NPs) are exposed to a nucleating agent, and then undergo controlled sulfidation to produce $Ag/Ag_2S$ core-shell structures, resulting in a slower dissolution rate without the loss of anti-biofouling performance.

Methods of producing coatings comprising the above-described $Ag/Ag_2S$ core-shell structures are provided herein. In some embodiments, a method may comprise obtaining a substrate having a surface, and exposing the surface to a plurality of silver nanoparticles (Ag NPs).

In certain embodiments, the substrate may be selected from the group consisting of a water treatment instrument, a surgical instrument, an implantable medical device, a catheter, a bandage, a furniture article, a garment, portions thereof, and combinations thereof. In some embodiments, the substrate may comprise a material selected from the group consisting of a metal, a metal alloy, a polymer, a membrane, a textile, and combinations thereof. Non-limiting examples of substrates include stainless steel, a nickel-chromium alloy, and titanium. In an embodiment, the substrate may comprise stainless steel.

The method may further comprise applying a nucleating agent to the silver nanoparticles to form a plurality of silver cores. In some embodiments, the nucleating agent may be selected from the group consisting of sodium borohydride, hydrazine, D-glucose, hyaluronic acid, and combinations thereof. In an embodiment, the nucleating agent may be D-glucose. Table 1 below includes some examples of suitable nucleating agents:

TABLE 1

| Nucleating agent | Formula | Toxicity Class |
|---|---|---|
| Sodium borohydride | $NaBH_4$ | 3 |
| Hydrazine | $N_2H_4$ | 4 |
| D-glucose | $C_6H_{12}O_6$ | 0 |
| Hyaluronic acid | $C_{14}H_{21}NO_{11}$ | 0 |

In certain embodiments, the nucleating agent may have a concentration from about 3 mM to about 300 mM. The nucleating agent may have a concentration of, for example, about 3 mM, about 5 mM, about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 20 mM, about 210 mM, about 220 mM, about 230 mM, about 240 mM, about 250 mM, about 260 mM, about 270 mM, about 280 mM, about 290 mM, about 300 mM, or any range between any two of these values, including endpoints.

The method may still further comprise passivating the silver cores by applying a sulfidation agent to the silver cores to form silver sulfide ($Ag_2S$) shells around the silver cores, thereby forming a coating comprising a plurality of sulfidated silver nanoparticles ($Ag/Ag_2S$) having a core-shell structure. In some embodiments, the plurality of sulfidated silver nanoparticles may be uniformly or substantially uniformly distributed on the surface.

In certain embodiments, the sulfidation agent may be selected from the group consisting of sodium sulfide, sodium thiosulfate, thiocarbamide, thioacetamide, and combinations thereof. In an embodiment, the sulfidation agent may comprise sodium sulfide. Table 2 below includes some examples of suitable sulfidation agents:

TABLE 2

| Sulfidation agent | Formula | Toxicity Class |
|---|---|---|
| Sodium sulfide | $Na_2S$ | 3 |
| Sodium thiosulfate | $Na_2S_2O_3$ | 1 |
| Thiocarbamide | $SC(NH_2)_2$ | 3 |
| Thioacetamide | $C_2H_5NS$ | 2 |

In some embodiments, the sulfidation agent may have a concentration from about $10^{-1}$ M to about $10^{-5}$ M. The sulfidation agent may have a concentration of, for example, about $10^{-1}$ M, about $10^{-2}$ M, about $10^{-3}$ M, about $10^{-4}$ M, about $10^{-5}$ M, or any range between any two of these values, including endpoints.

In certain embodiments, the sulfidation agent may be applied to the silver cores for a time period of from about 1 hour to about 12 hours. The time period may be, for example, about 1 hour, about 2 hours, about 3 hours, about 4 hours, about 5 hours, about 6 hours, about 7 hours, about 8 hours, about 9 hours, about 10 hours, about 11 hours, about 12 hours, or any range between any two of these values, including endpoints.

In certain embodiments, the silver cores may have a diameter from about 10 nm to about 100 nm. The diameter may be an average diameter or a maximum or minimum diameter. The silver cores may have a diameter of, for example, about 10 nm, about 20 nm, about 30 nm, about 40 nm, about 50 nm, about 60 nm, about 70 nm, about 80 nm, about 90 nm, about 100 nm, or any range between any two of these values, including endpoints.

In some embodiments, a coating as described herein may be formed by the methods described herein. The coating may be formed on or applied to one or more substrates, as described herein. In certain embodiments, a composition may comprise a plurality of sulfidated silver nanoparticles having a core-shell structure, as described herein. In some embodiments, a substrate as described herein may have a surface coated with (i.e., coated by) a composition comprising a plurality of sulfidated silver nanoparticles having a core-shell structure, as described herein.

The coatings and methods described herein may be used for a number of substrates and applications. In one example, the coatings may be applied in situ in systems prone to biofouling, such as water processor waste tanks, without the need for shutdown or disassembly. In other examples, the coatings may be applied to medical devices or hospital equipment to provide reduced silver leaching and long-term antimicrobial properties.

Embodiment 1 is a method comprising: obtaining a substrate having a surface; exposing the surface to a plurality of silver nanoparticles (Ag NPs); applying a nucleating agent to the silver nanoparticles to form a plurality of silver cores; and passivating the silver cores by applying a sulfidation agent to the silver cores to form silver sulfide (Ag$_2$S) shells around the silver cores; thereby forming a coating comprising a plurality of sulfidated silver nanoparticles (Ag/Ag$_2$S) having a core-shell structure.

Embodiment 2 is the method of embodiment 1, wherein the plurality of sulfidated silver nanoparticles are uniformly distributed on the surface.

Embodiment 3 is the method of embodiment 1 or 2, wherein the substrate is selected from the group consisting of a water treatment instrument, a surgical instrument, an implantable medical device, a catheter, a bandage, a furniture article, a garment, and combinations thereof.

Embodiment 4 is the method of any of embodiments 1-3, wherein the substrate comprises a material selected from the group consisting of a metal, a metal alloy, a polymer, a membrane, a textile, and combinations thereof.

Embodiment 5 is the method of any of embodiments 1-4, wherein the substrate comprises stainless steel.

Embodiment 6 is the method of any of embodiments 1-5, wherein the nucleating agent is selected from the group consisting of sodium borohydride, hydrazine, D-glucose, hyaluronic acid, and combinations thereof.

Embodiment 7 is the method of any of embodiments 1-5, wherein the nucleating agent is D-glucose.

Embodiment 8 is the method of any of embodiments 1-7, wherein the nucleating agent has a concentration from about 3 mM to about 300 mM.

Embodiment 9 is the method of any of embodiments 1-8, wherein the sulfidation agent is selected from the group consisting of sodium sulfide, sodium thiosulfate, thiocarbamide, thioacetamide, and combinations thereof.

Embodiment 10 is the method of any of embodiments 1-8, wherein the sulfidation agent is sodium sulfide.

Embodiment 11 is the method of any of embodiments 1-10, wherein the sulfidation agent has a concentration from about 10$^{-1}$ M to about 10$^{-5}$ M.

Embodiment 12 is the method of any of embodiments 1-11, wherein applying the sulfidation agent to the silver cores is done for a time period of from about 1 hour to about 12 hours.

Embodiment 13 is the method of any of embodiments 1-12, wherein the silver cores have a diameter from about 10 nm to about 100 nm.

Embodiment 14 is a coating formed by the method of any of embodiments 1-13.

Embodiment 15 is a composition comprising a plurality of sulfidated silver nanoparticles having a core-shell structure.

Embodiment 16 is a substrate having a surface coated with the composition of embodiment 15.

Embodiment 17 is the substrate of embodiment 16, wherein the plurality of sulfidated silver nanoparticles are uniformly distributed on the surface.

Embodiment 18 is the substrate of embodiment 16 or 17, wherein the substrate is selected from the group consisting of a water treatment instrument, a surgical instrument, an implantable medical device, a catheter, a bandage, a furniture article, a garment, and combinations thereof.

Embodiment 19 is the substrate of any of embodiments 16-18, wherein the substrate comprises a material selected from the group consisting of a metal, a metal alloy, a polymer, a membrane, a textile, and combinations thereof.

Embodiment 20 is the substrate of any of embodiments 16-18, wherein the substrate comprises stainless steel.

EXAMPLES

Example 1: Anti-Biofouling Performance of Sulfidated Silver Nanoparticles

Figure 2:
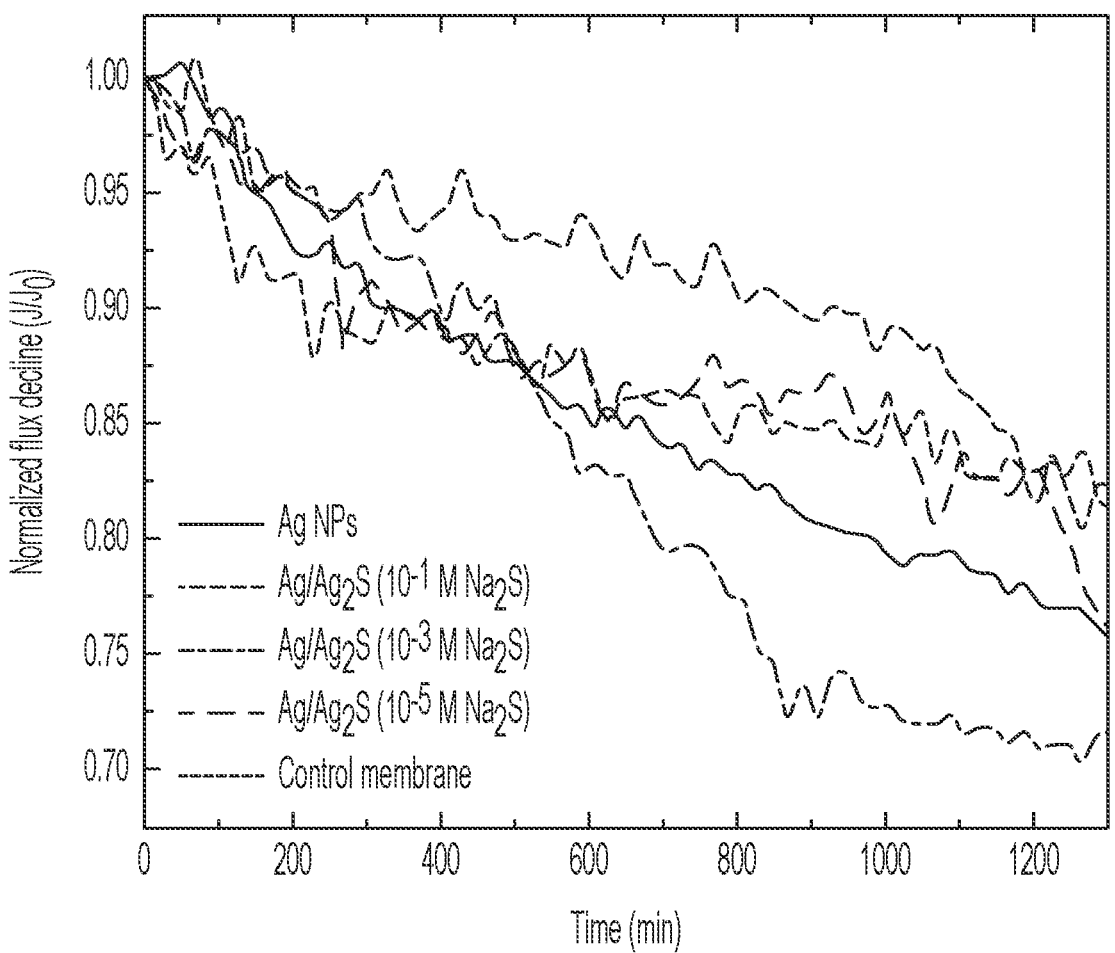
FIG. 2 is a graph showing the results of preliminary research evaluating the anti-biofouling performance of Ag NPs and $Ag/Ag_2S$ core-shell structures, as described herein.

FIG. 2 is a graph showing the results of preliminary research evaluating the anti-biofouling performance of Ag NPs and Ag/Ag$_2$S core-shell structures, as described herein, which were passivated using different concentrations of a sulfidation agent (sodium sulfide (Na$_2$S)) when applied to a reverse-osmosis membrane system. In particular, the graph shows the normalized flux decline over time for membranes coated with: Ag NPs, Ag/Ag$_2$S core-shell structures sulfidated with 10$^{-1}$ M Na$_2$S, Ag/Ag$_2$S core-shell structures sulfidated with 10$^{-3}$ M Na$_2$S, Ag/Ag$_2$S core-shell structures sulfidated with 10$^{-5}$ M Na$_2$S, as compared to the control membrane. Biofouling resistance is indicated by the lower flux decline in the membranes coated with Ag/Ag$_2$S core-shell structures. Despite an 85% decrease in silver release rate, the Ag/Ag$_2$S core-shell structures were found to be more effective than the pristine Ag NPs for biofouling control in desalination models, a performance that was attributed to the longer retention of silver on the coated surfaces. These results demonstrate that partially sulfidated Ag NPs have better anti-fouling performance compared to pristine Ag NP-based coatings in dynamic systems.

Example 2: Optimal Level of Sulfidation (Ag:S Ratio)

To determine the optimal level of sulfidation (i.e., the optimal Ag:S ratio) that maintains the biofouling resistance of the coatings described herein, stainless steel (SS) was used as a model surface for treatment. In a batch system, stainless steel coupons (10 mm diameter×2 mm thickness) were immersed in deionized water with 50 mM silver nitrate (AgNO$_3$). Then, a nucleation agent (sodium borohydride (NaBH$_4$)), was added to concentrations of 3 mM, 30 mM, and 300 mM. The functionalized surfaces were rinsed in deionized water to remove unbound or weakly attached NPs from the stainless steel surface. The functionalized surfaces were then exposed to a solution with a sulfidation agent (sodium sulfide (Na$_2$S)) to form an Ag$_2$S shell over the Ag NPs. Different concentrations of the sulfidation agent (ranging from 10$^{-5}$ to 10$^{-1}$ M) and different exposure times (between 1 hour and 12 hours) were used to generate Ag/Ag$_2$S core-shell structures with different levels of sulfidation (expressed as different Ag:S ratios).

The morphology of the Ag NPs attached to the stainless steel was characterized by scanning electron microscopy (SEM). The SEM was equipped with a backscattered electron detector for improved visualization of Ag NPs on the surface. The SEM showed the presence of Ag NPs and sulfur. Energy dispersive X-Ray (EDX) analysis was also performed.

Figure 3A:
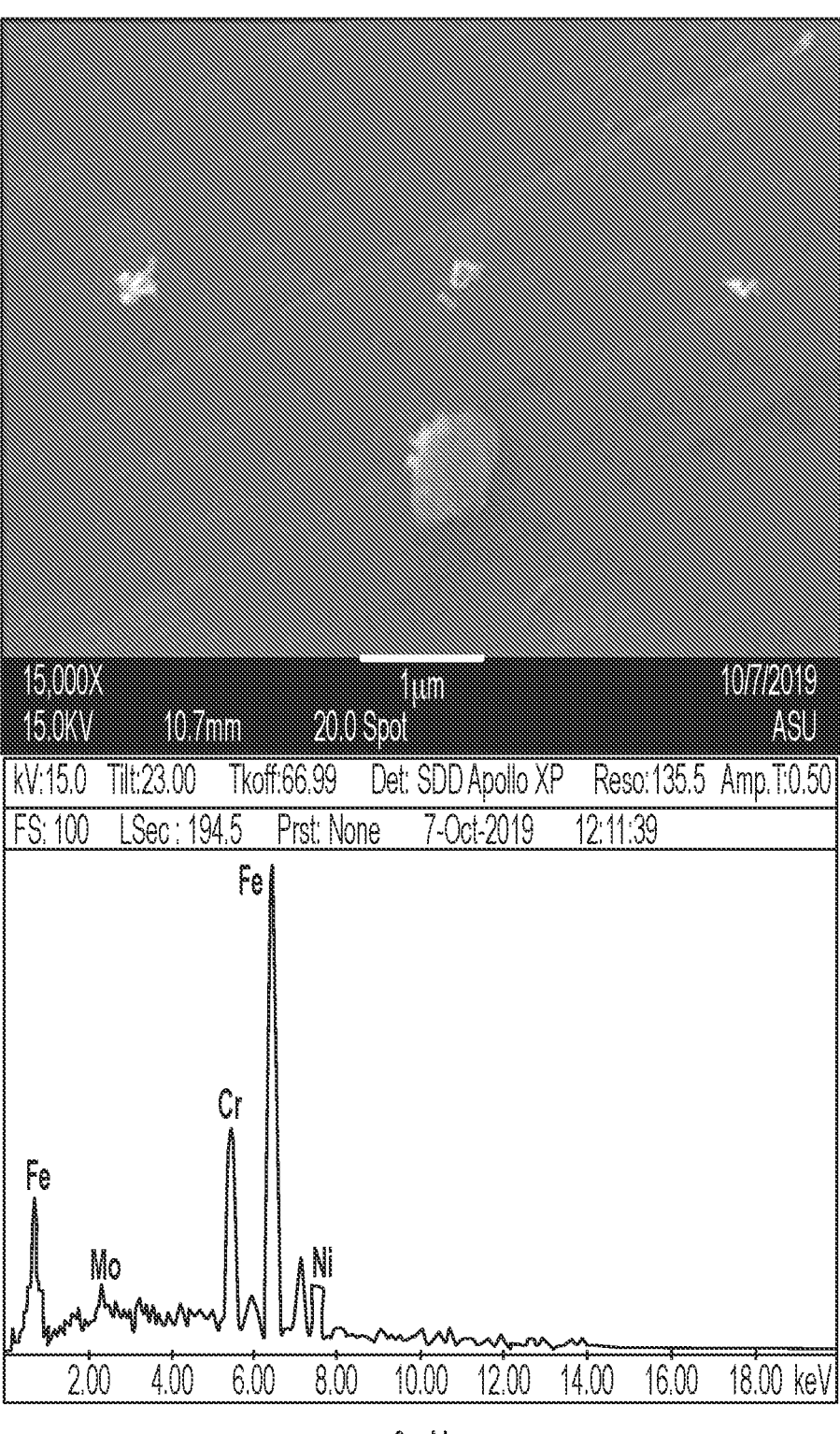
FIG. 3A shows an SEM image (top) and an EDX analysis (bottom) of a stainless steel substrate having Ag NPs with a nucleation agent added to a concentration of 3 mM.
Figure 3B:
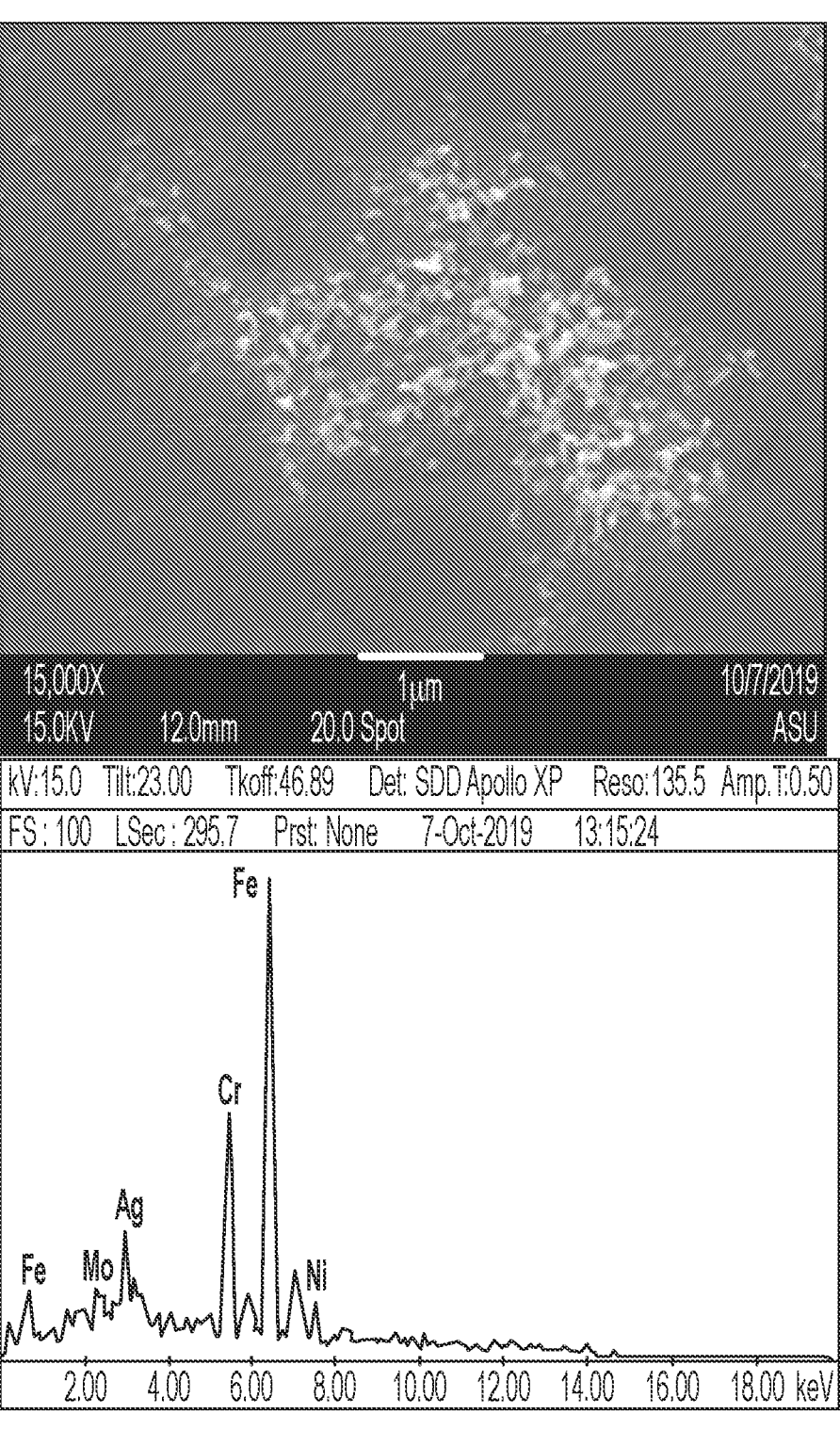
FIG. 3B shows an SEM image (top) and an EDX analysis (bottom) of a stainless steel substrate having Ag NPs with a nucleation agent added to a concentration of 30 mM.
Figure 3C:
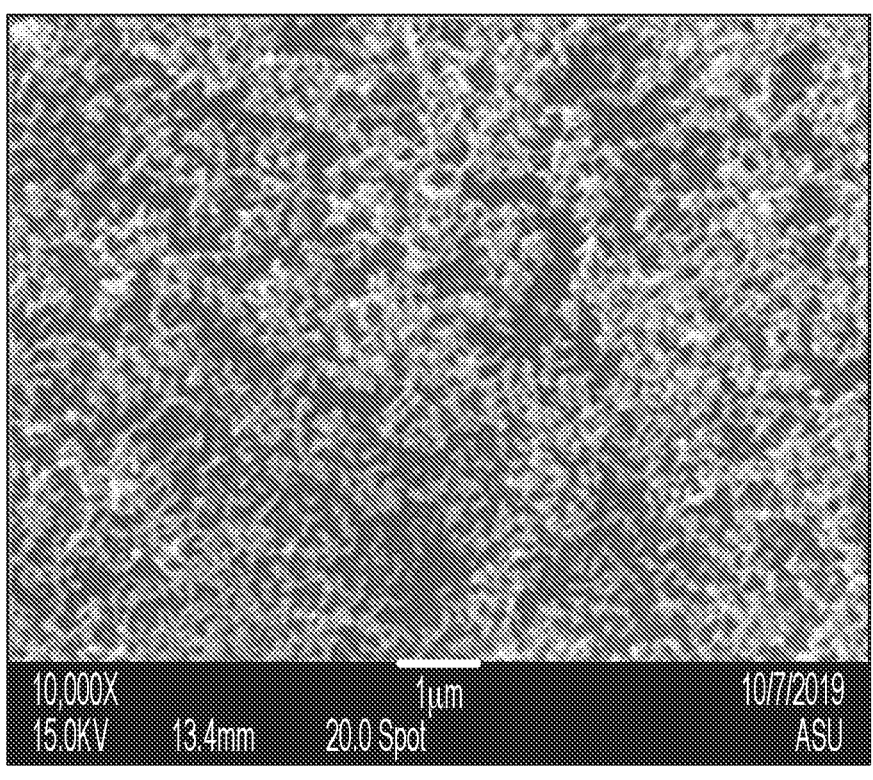
FIG. 3C shows an SEM image (top) and an EDX analysis (bottom) of a stainless steel substrate having Ag NPs with a nucleation agent added to a concentration of 300 mM.
Figure 3C:
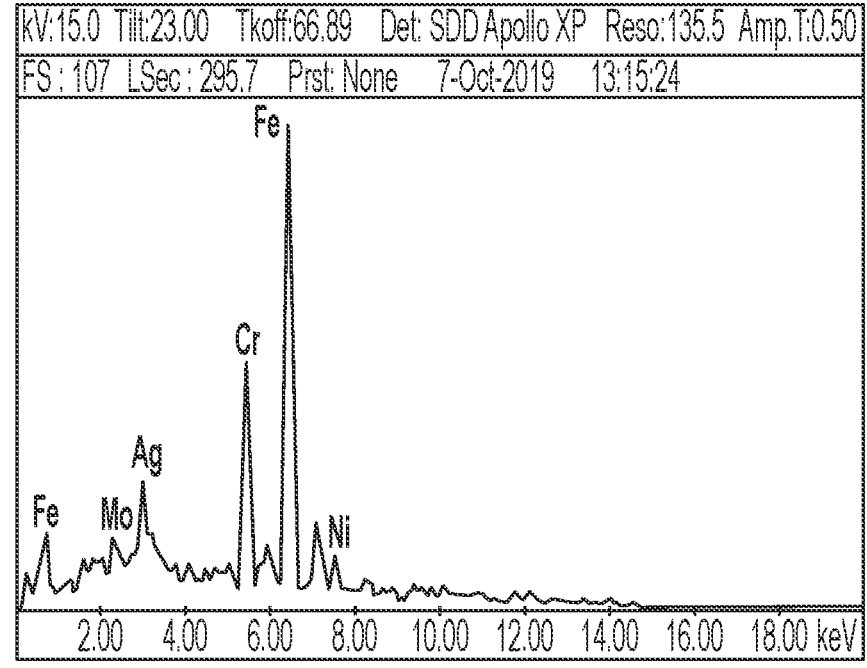

FIG. 3A, FIG. 3B, and FIG. 3C show SEM images (top) and EDX analyses (bottom) of the stainless steel having Ag NPs with a nucleation agent (sodium borohydride (NaBH$_4$)) added to concentrations of 3 mM, 30 mM, and 300 mM, respectively. The snowflake-like structure of the Ag NPs is evident in the SEM images of FIG. 3A, FIG. 3B, and FIG.

3C; the presence of silver (Ag) is evident in the EDX analyses shown in FIG. 3A, FIG. 3B, and FIG. 3C.

Figure 4A:
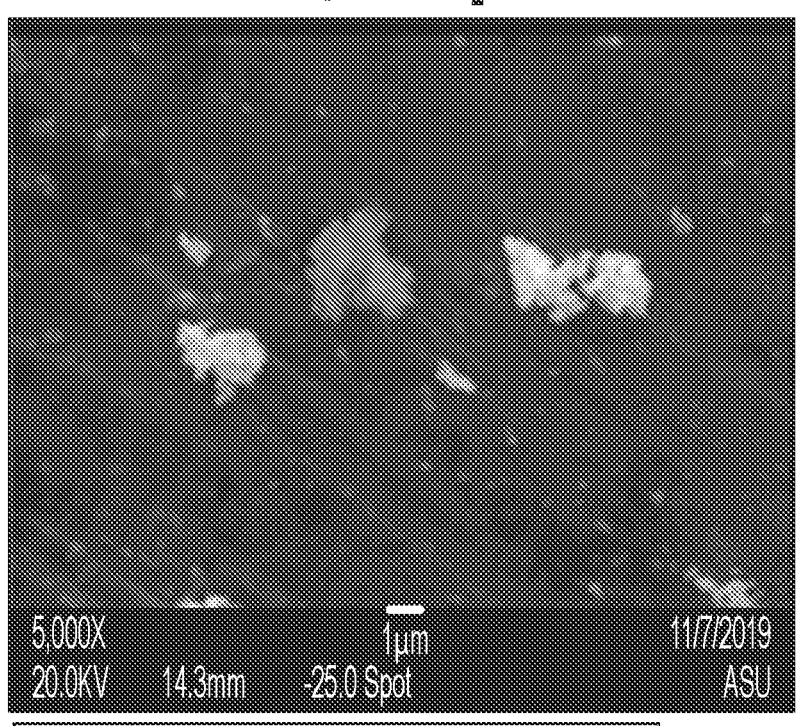
FIG. 4A shows an SEM image (top) and an EDX analysis (bottom) of $Ag/Ag_2S$ core-shell structures sulfidated with $10^{-1}$ M $Na_2S$.
Figure 4A:
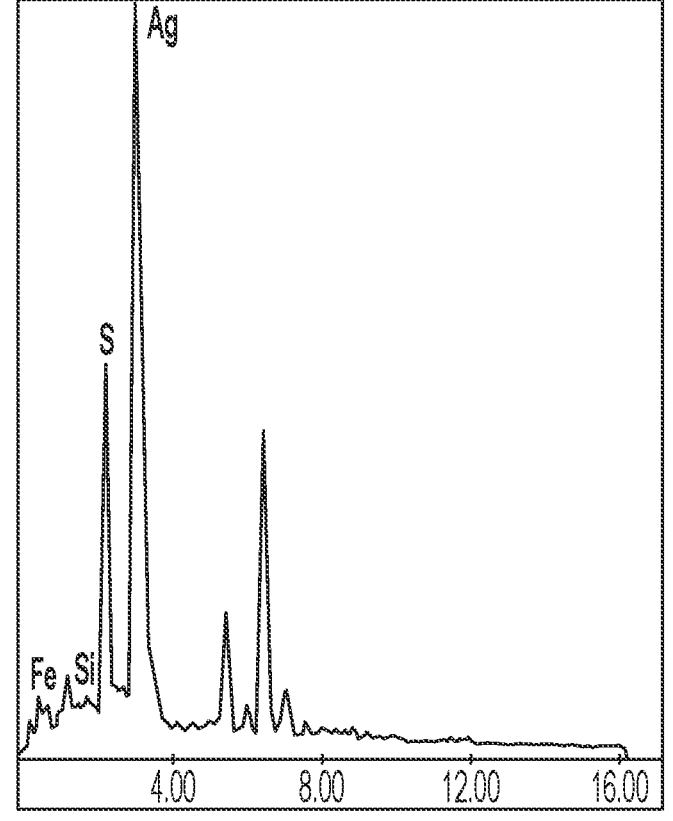
Figure 4B:
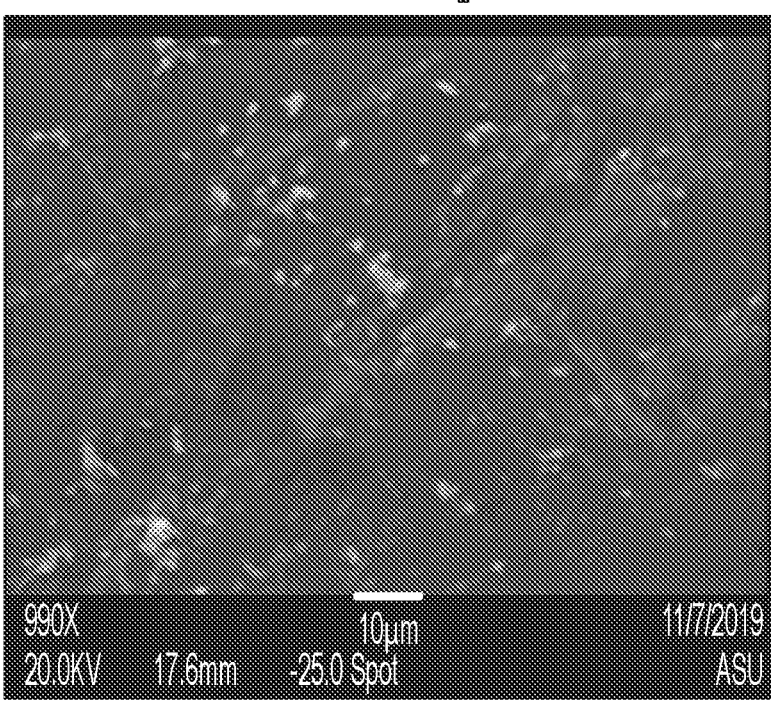
FIG. 4B shows an SEM image (top) and an EDX analysis (bottom) of $Ag/Ag_2S$ core-shell structures sulfidated with $10^{-3}$ M $Na_2S$.
Figure 4B:
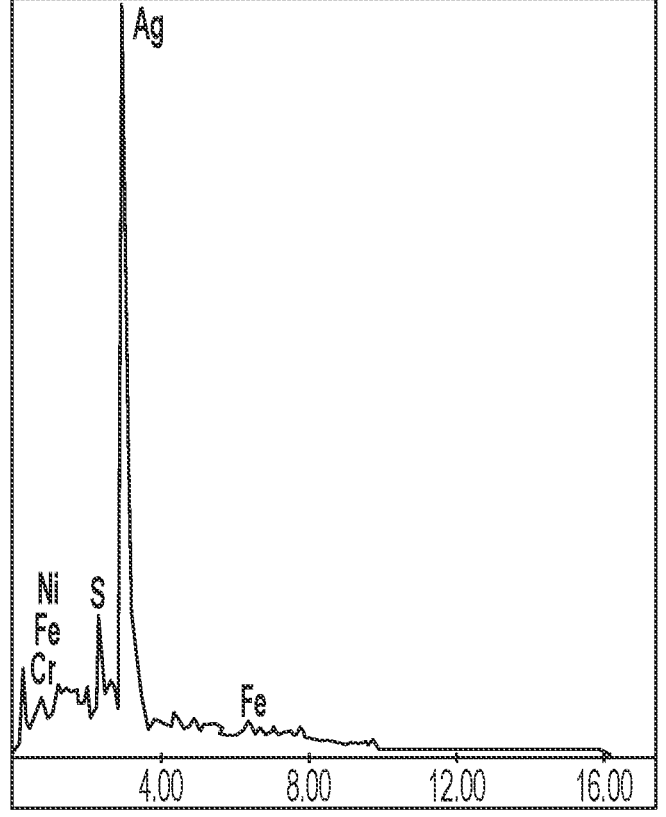
Figure 4C:
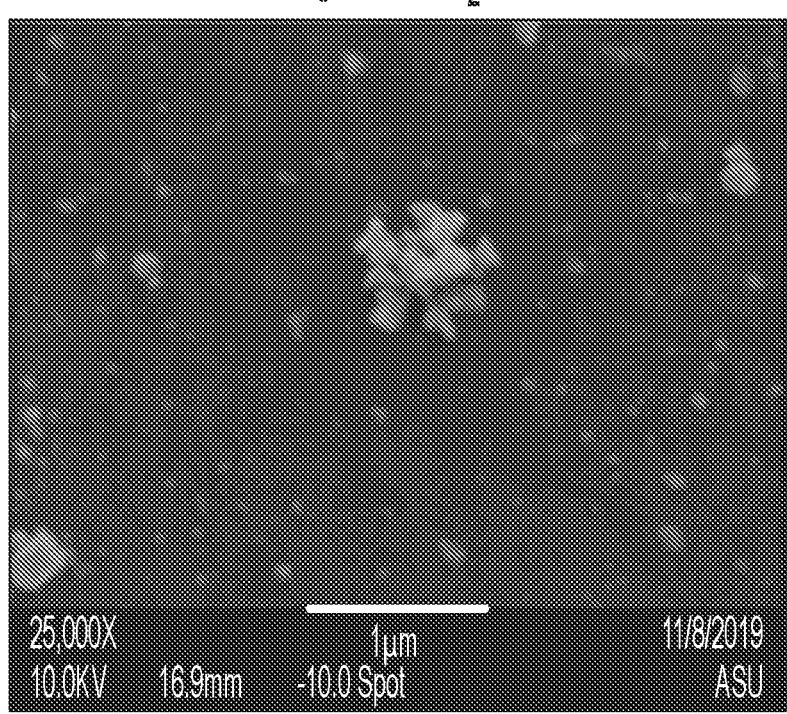
FIG. 4C shows an SEM image (top) and an EDX analysis (bottom) of $Ag/Ag_2S$ core-shell structures sulfidated with $10^{-5}$ M $Na_2S$.
Figure 4C:
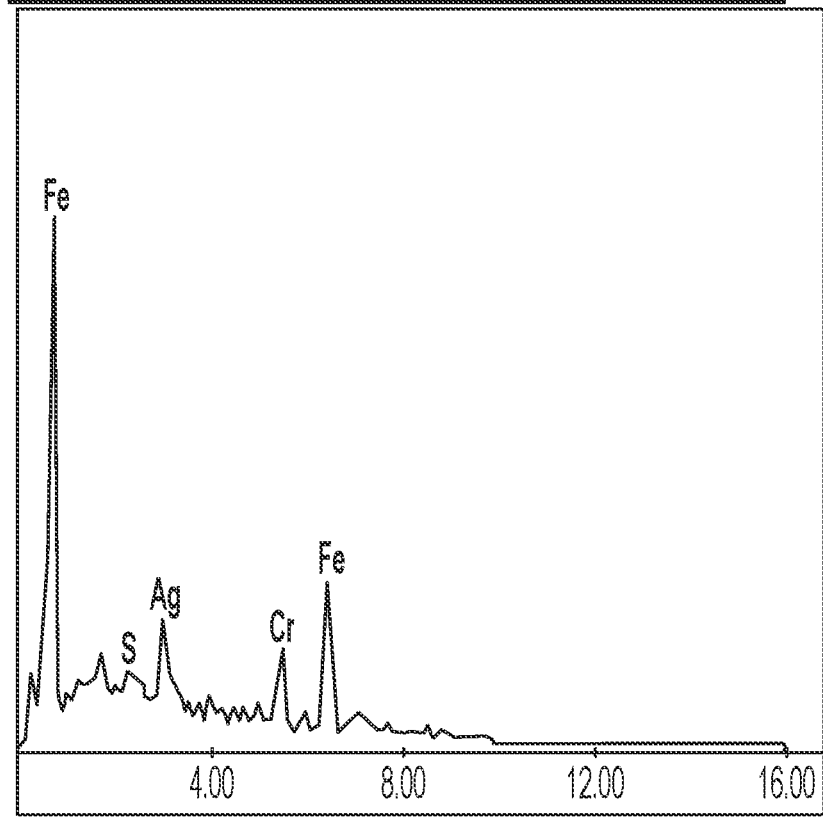
Figure 4D:
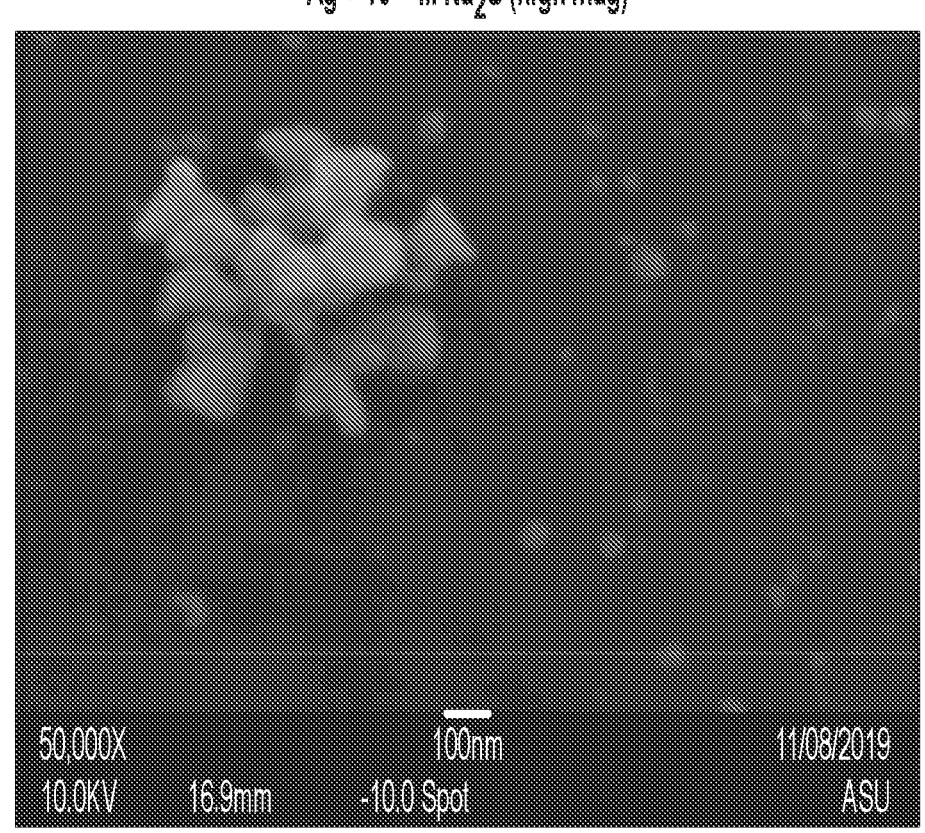
FIG. 4D shows the SEM image of FIG. 4C at a higher magnification.

FIG. 4A, FIG. 4B, and FIG. 4C show SEM images (top) and EDX analyses (bottom) of $Ag/Ag_2S$ core-shell structures sulfidated with $10^{-1}$ M $Na_2S$, $10^{-3}$ M $Na_2S$, and $10^{-5}$ M $Na_2S$, respectively. The SEM images of FIG. 4A, FIG. 4B, and FIG. 4C show sulfidated (i.e., passivated) Ag NPs, and the corresponding EDX analysis confirm the presence of sulfur (S). FIG. 4D shows the SEM image of FIG. 4C at a higher magnification.

Example 3: Antimicrobial Activity of Functionalized Surfaces

The biofilm-forming bacterial model *Pseudomonas aeruginosa* (ATCC 25668) was used to verify bacterial inactivation by silver-coated surfaces in static antimicrobial assays. Pristine (i.e., non-functionalized) and functionalized Ag NP coatings on stainless steel (SS) coupons were exposed to a suspension of *P. aeruginosa* (107 Colony Forming Units/mL (CFU/mL)) in a simple sterile saline solution (0.9% NaCl). The functionalized Ag NP coatings were exposed a nucleation agent added to concentrations of 3 mM, 30 mM, and 300 mM (expressed as "silver concentration").

Figure 5:
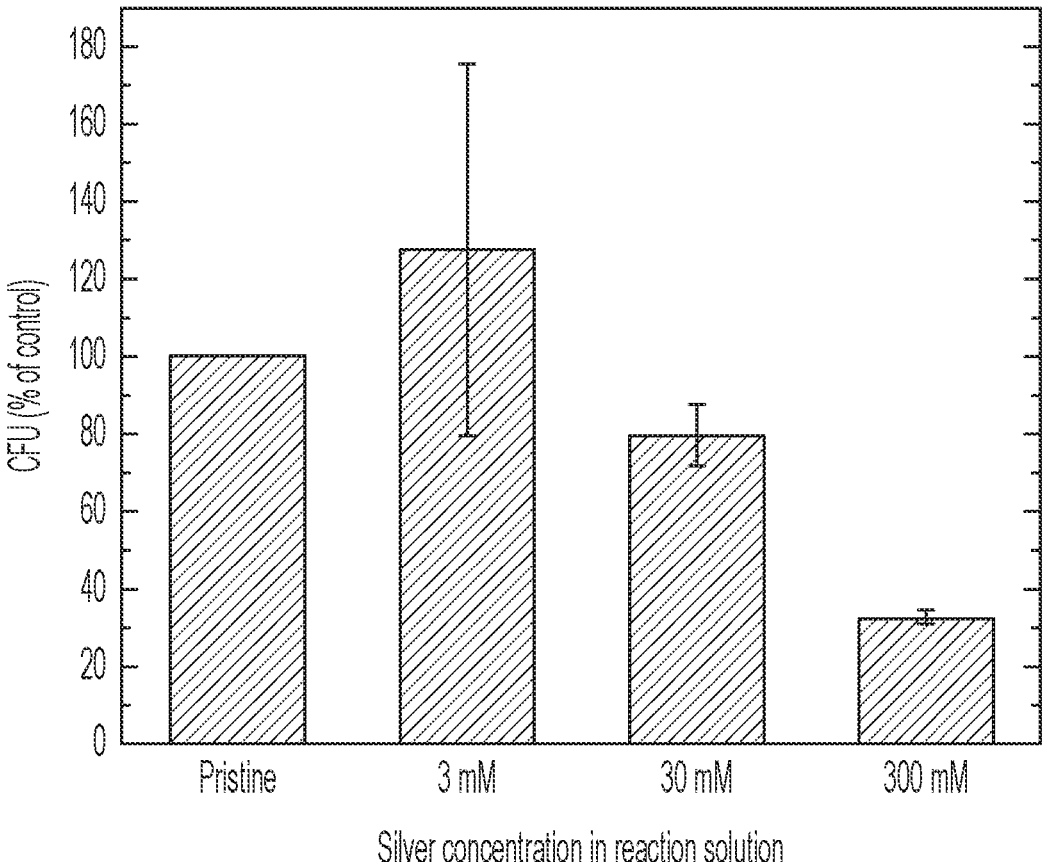
FIG. 5 is a graph showing the antimicrobial activity of pristine and functionalized (3 mM, 30 mM, and 300 mM) Ag NPs.

After 3 hours of contact, the cells were stained with Syto9 and propidium iodide (PI) for live and dead staining, respectively, and counted using an epifluorescence microscope. FIG. 5 is a graph showing the CFU counts (i.e., % of control) for the pristine, 3 mM, 30 mM, and 300 mM samples, demonstrating their respective antimicrobial activity. The results demonstrate decreasing bacterial viability with increasing silver loading, with the 300 mM samples having the best antimicrobial performance.

Example 4: Biofilm Development on Functionalized Surfaces

Figure 6:
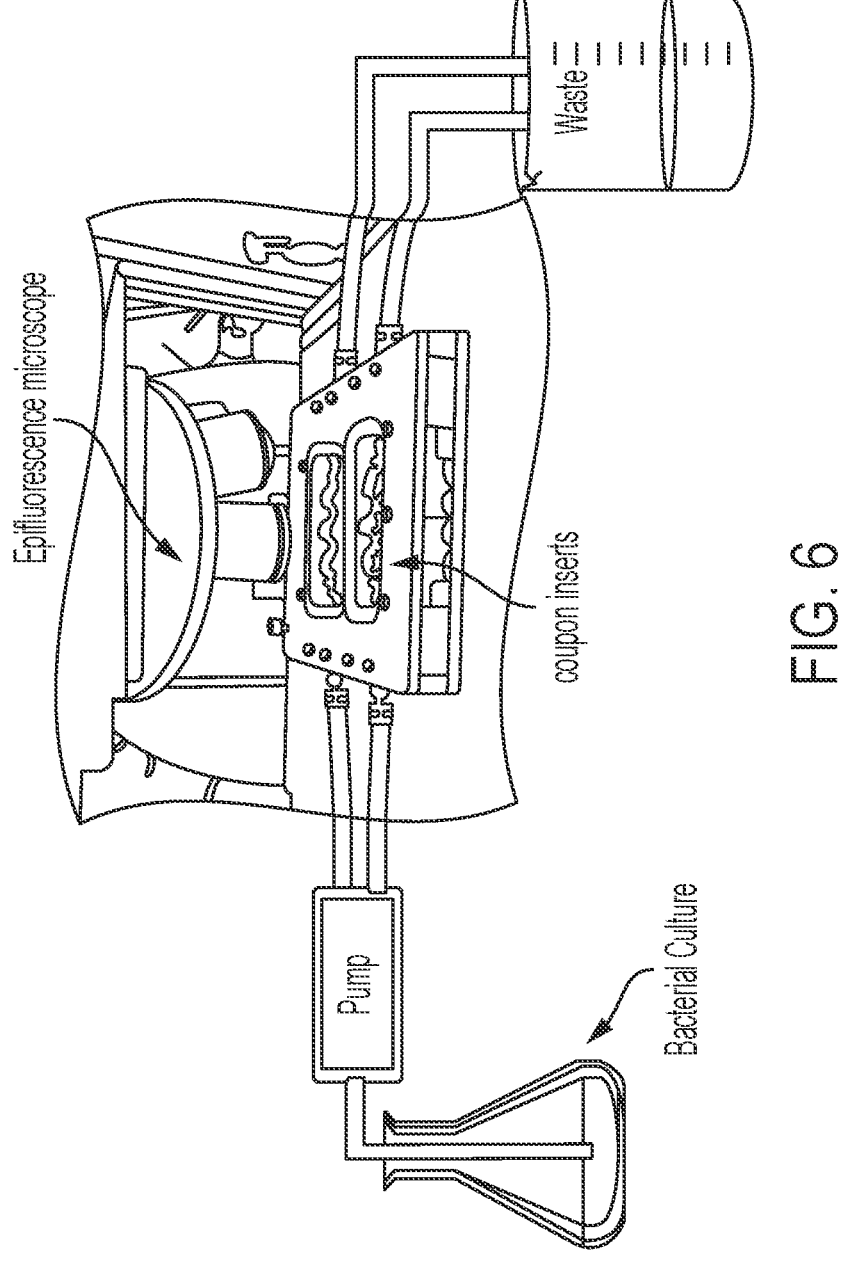
FIG. 6 shows a schematic representation of the experimental setup described herein.

The rate of biofilm formation will be monitored using a microscopy flow cell designed to hold coupons (10 mm diameter×2 mm thickness). A peristaltic pump will be used to circulate a synthetic growth medium supplemented with *P. aeruginosa* ($10^6$ Colony Forming Units/mL (CFU/mL)). The rate of cell deposition on the surface will be evaluated by total reflected light microscopy on an epifluorescence microscope. FIG. 6 shows a schematic representation of the experimental setup. Biofilm formation rates will be quantified using optical coherence tomography (OCT) and biovolume image analysis. Functionalized Ag NPs are expected to inhibit biofilm development more effectively than pristine Ag NPs.

Example 5: Nucleation of Ag NPs and $Ag/Ag_2S$ Core-Shell Structures of Different Sizes First, Ag NPs were formed as described in Example 2 above. Then, silver nitrate (10 mM) and sodium borohydride (1 mM) were added to grow the Ag NPs. The resulting Ag NPs ranged from about 10 nM to about 100 nM in diameter. Stainless steel surfaces functionalized with the Ag NPs were then exposed to a sodium sulfide ($Na_2S$) solution to form $Ag/Ag_2S$ core-shell structures. Different concentrations of sodium sulfide (ranging from $10^{-5}$ M to $10^{-1}$ M) and different exposure times (from 1 hour to 12 hours) were used to generate $Ag/Ag_2S$ core-shell structures having different levels of sulfidation (Ag:S ratios). In addition to D-glucose, a non-toxic nucleation agent was used instead of sodium borohydride ($NaHB_4$), resulting in different-sized particles with a lower concentration of $AgNO_3$, suggesting that a lower concentration of $AgNO_3$ may be used to form Ag NPs.

Example 6: Forming Ag/AgBr and Ag/AgI Core-Shell Structures

The particle size of Ag NPs formed on a stainless steel surface may be controlled by seed-assisted growth. First, Ag NPs were formed as described in Example 2 above. Then, silver nitrate (10 mM) and sodium borohydride (1 mM) were added to grow the Ag NPs. Stainless steel surfaces functionalized with the Ag NPs were then exposed to sodium bromide (NaBr) and sodium iodide (NaI) solutions to form AgBr and AgI shells, respectively, over the Ag NPs. Different concentrations (ranging from $10^{-5}$ M to $10^{-1}$ M) were used to generate Ag/AgBr and Ag/AgI core-shell structures having different Ag:halide ratios.

Figure 7:
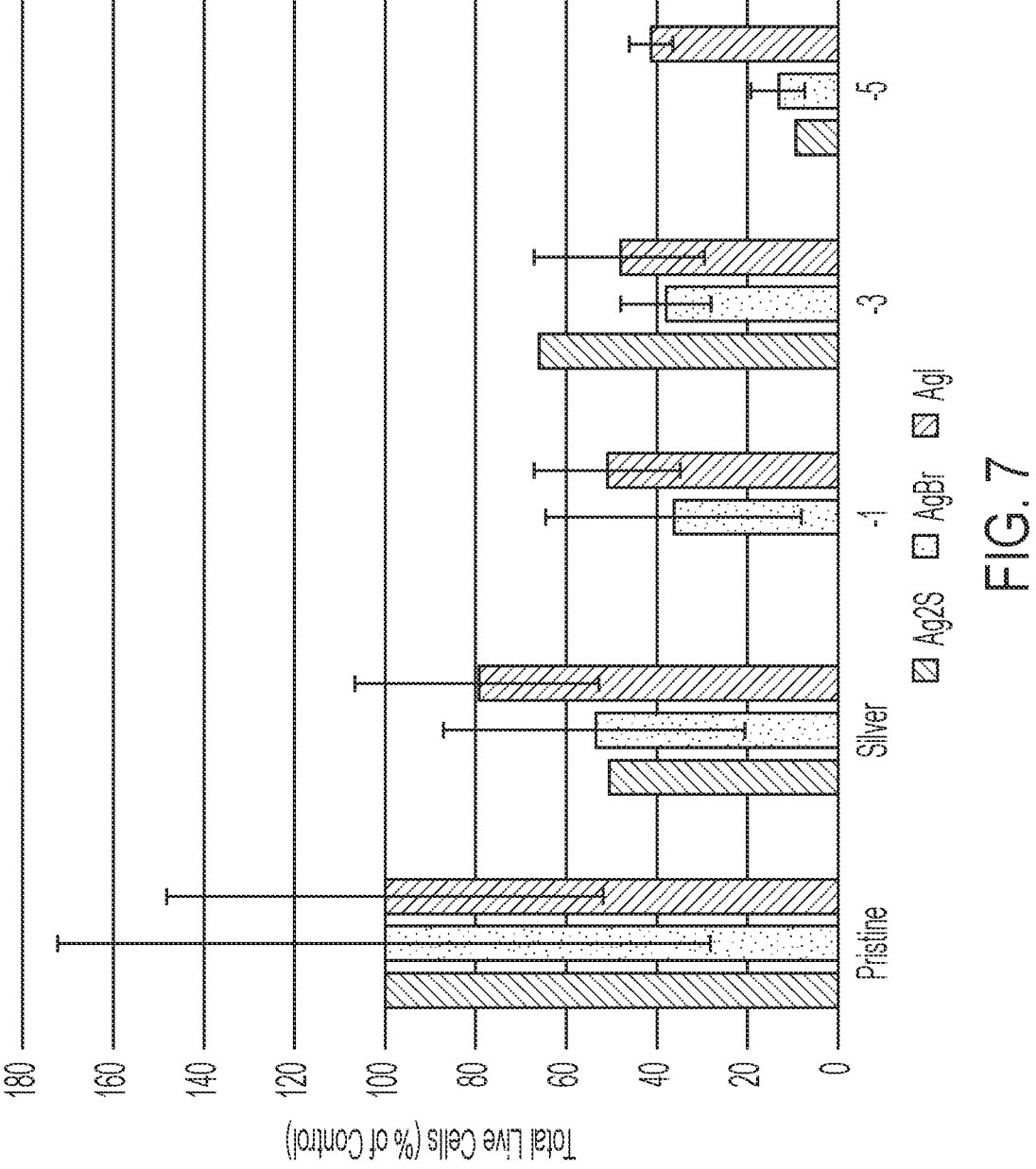
FIG. 7 shows the total live cells (i.e. % of control) of stainless steel surfaces coated with various iterations of Ag/S, Ag/Br, and Ag/I, as described herein.

The pristine, Ag/S, Ag/Br, and Ag/I-coated stainless steel surfaces were then exposed to *P. aeruginosa* for 3 hours of contact time, and the total live cells were determined by epifluorescence microscopy. FIG. 7 shows the total live cells (i.e. % of control) of pristine stainless steel surfaces that were coated with: (i) pristine Ag/S, Ag/Br, and Ag/I, (ii) functionalized Ag/S, Ag/Br, and Ag/I, (iii) Ag/S, Ag/Br, and Ag/I core-shell structures passivated with concentrations of $10^{-5}$ M, (iv) Ag/S, Ag/Br, and Ag/I core-shell structures passivated with concentrations of $10^{-3}$ M, and (v) Ag/S, Ag/Br, and Ag/I core-shell structures passivated with concentrations of $10^{-1}$ M (left to right). The $Ag/Ag_2S$ core-shell structures showed better antimicrobial performance than the Ag:halide compositions.

To determine the effects of size and Ag:halide ratio on biofouling resistance, the rate of biofilm formation was quantified using optical coherence tomography (OCT) and biovolume image analysis. Ag/Br appeared to have higher antimicrobial activity compared to Ag/I, likely due to its higher solubility. The $10^{-5}$ M passivation treatment appeared to have the best static antimicrobial performance.

Figure 8:
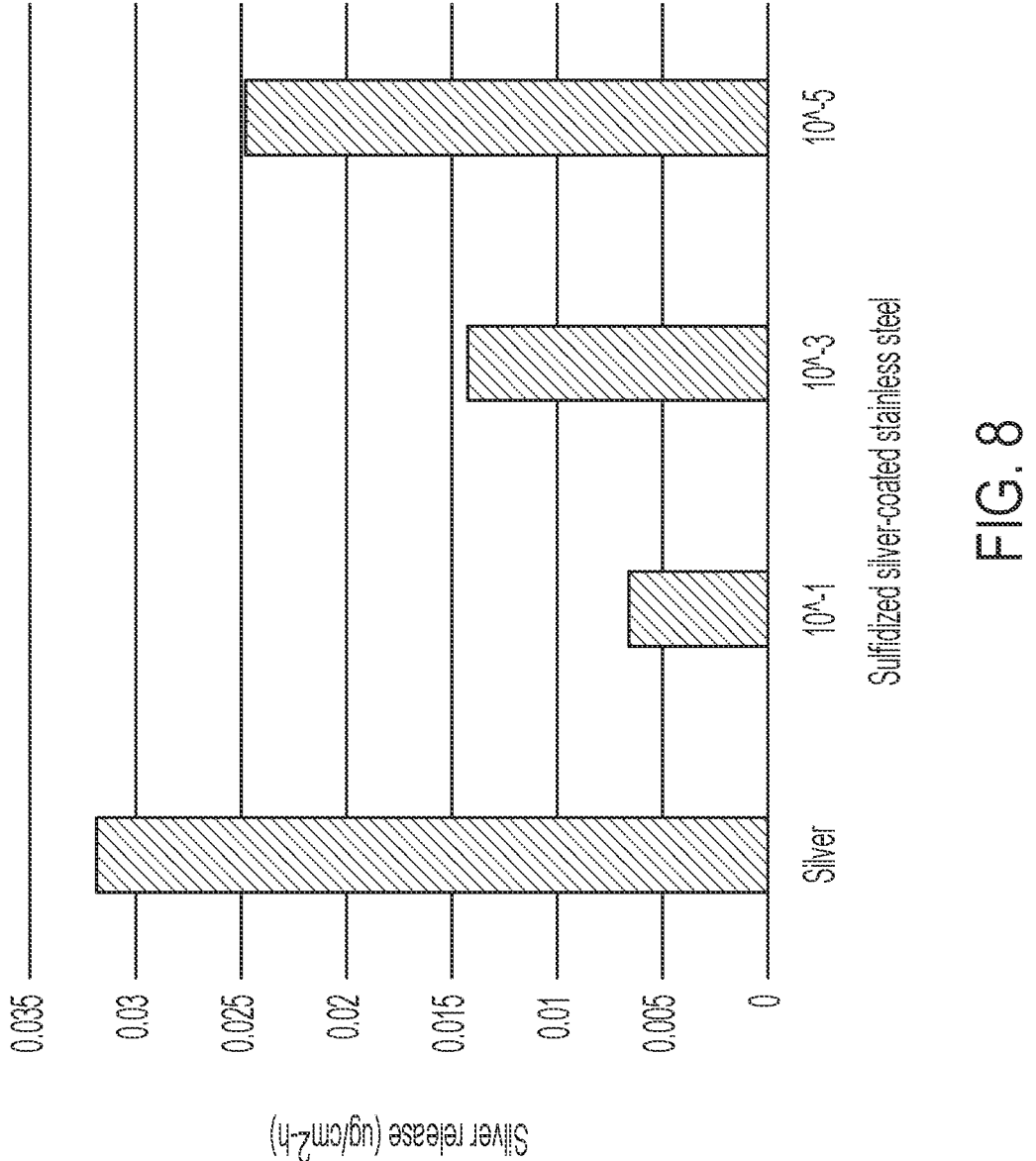
FIG. 8 shows silver release rate of different sulfidated silver-coated stainless steel surfaces, as described herein.

Example 7: Quantifying the Rate of Silver Release from Coatings with Different Sizes of Ag NPs First, coupons of functionalized stainless steel were prepared as described in Example 2 above. The coupons were then placed in 50 mL sealed acid-washed polypropylene tubes. A 40 mL volume of synthetic potable water solution was placed in the tubes, and the tubes were sealed. The tubes were continuously agitated using a benchtop orbital shaker. Each day, a sample was removed to quantify the amount of silver leached into the water, and the amount of silver remaining on the coupon. The experiment was continued until the rate of silver release was close to zero and the surfaces were depleted of their silver content. The results were analyzed using inductively coupled plasma-optical emission spectrometry (ICP-OES). FIG. 8 shows the silver release rate from the different sulfidated silver-coated stainless steel surfaces, as determined by ICP-OES. Silver release appears to decrease with the degree of sulfidation.

Example 8: Comparison of Nucleation Agents

FIG. 9A and FIG. 9B show surfaces exposed to compositions using D-glucose and sodium borohydride ($NaHB_4$), respectively, as nucleation agents. The surface exposed to D-glucose maintains an apparent cloudy layer, while the surface exposed to sodium borohydride is as shiny as it was before it was coated.

Ag NP nucleation and Ag/Ag$_2$S passivation conditions were established using D-glucose, as described herein. In addition to D-glucose, a non-toxic nucleation agent was used instead of sodium borohydride (NaHB$_4$), resulting in different-sized particles with a lower concentration of AgNO$_3$. FIG. 10A, FIG. 10B, and FIG. 10C show SEM images of Ag NPs exposed to D-glucose as a nucleation agent. The SEM images suggest better uniformity, with one order less of AgNO$_3$ consumption.

Example 9: Modeling and Predicting Rates of Silver Release from Complex Silver Coatings The silver release kinetic model of Liu and Hurt will be modified to include descriptors of the Ag/Ag$_2$S core-shell structures described herein:

$$-\frac{1}{m}\frac{dm}{dt} = A\beta e^{-\frac{E}{RT}}\left(\frac{[H^+]}{10^{-7}M}\right)^{0.18}$$

Where m is the mass of silver, A is the surface area normalized silver dissolution rate constant (in µg-released day$^{-1}$ m$^{-2}$), β is a descriptor linked ratio between the surface area normalized sulfur content and the particle volume, and E=77 kJmol−1. By normalizing both the rate of silver release and the sulfur content to the particle size and surface area, the effect of both particle size and Ag$_2$S layer will be taken into account. The value of each descriptor will be calibrated based on the experimental silver release data described in Example 7 above.

Example 10: In Situ Coating Procedures

To identify the synthesis conditions needed to achieve the desired nanoparticle size and composition in flow-through systems, a synthetic solution mimicking the composition of water in a potable water system ("synthetic water") will be circulated in a flow-through system over a 316 L stainless steel surface using a gear pump. The synthetic water will be supplemented with silver nitrate and the nucleation agent to form Ag NPs on the stainless steel surface. Then, the formed Ag NPs will be passivated using a sulfidation agent. The concentrations of nucleating and passivating reagents, as well as the silver nitrate concentration, will be varied to obtain Ag/Ag$_2$S core-shell structures of different nanoparticle sizes, compositions, and surface loading.

Example 11: Effect of Rate of Silver Deposition on Biofouling Performance

Compatibility between the proposed Ag/Ag$_2$S core-shell structure-based coatings and existing silver-based disinfection practices will be evaluated by measuring the rate of silver ion deposition on pristine stainless steel and Ag/Ag$_2$S core-shell structure-coated stainless steel. Functionalized coupons of stainless steel prepared as described in Example 2 above will be placed in 50 mL sealed acid-washed polypropylene tubes. A 40 mL volume of a synthetic solution mimicking the composition of water in a potable water system ("synthetic water") will be supplemented with 4 ppm of aqueous silver in the form of silver fluoride. The supplemented synthetic water will be placed in the tubes, and the tubes will be sealed. Tubes will be continuously agitated using a benchtop orbital shaker. Every day, a sample will be removed to quantify the amount of aqueous silver remaining in the solution. The experiment will continue until the rate of silver deposition is close to zero or the solution is depleted of its silver content.

To determine the effect of silver ion deposition on biofouling resistance, the rate of biofilm formation will be monitored during this experiment. Changes in anti-biofouling properties will be established by comparing Ag/Ag$_2$S core-shell structure-coated surfaces with the same surfaces exposed to a 4 ppm ionic silver solution for a period of time determined by the experiment and representative of the equilibrium level of silver deposition on the surface.

While the present disclosure has been illustrated by the description of exemplary embodiments thereof, and while the embodiments have been described in certain detail, the Applicant does not intend to restrict or in any way limit the scope of the appended claims to such detail. Additional advantages and modifications will readily appear to those skilled in the art. Therefore, the disclosure in its broader aspects is not limited to any of the specific details, representative devices and methods, and/or illustrative examples shown and described. Accordingly, departures may be made from such details without departing from the spirit or scope of the Applicant's general inventive concept.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Instead, this application is intended to cover any variations, uses, or adaptations of the present teachings and use its general principles. Further, this application is intended to cover such departures from the present disclosure as come within known or customary practice in the art to which these teachings pertain. Many modifications and variations can be made to the particular embodiments described without departing from the spirit and scope of the present disclosure as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. A method comprising:

obtaining a substrate having a surface;

exposing the surface to a plurality of silver nanoparticles (Ag NPs);

applying a nucleating agent to the silver nanoparticles to form a plurality of silver cores; and passivating the silver cores by applying a sulfidation agent to the silver cores to form silver sulfide ($Ag_2S$) shells around the silver cores;

thereby forming a coating comprising a plurality of sulfidated silver nanoparticles ($Ag/Ag_2S$) having a core-shell structure.

2. The method of claim 1, wherein the plurality of sulfidated silver nanoparticles are uniformly distributed on the surface.

3. The method of claim 1, wherein the substrate is selected from the group consisting of a water treatment instrument, a surgical instrument, an implantable medical device, a catheter, a bandage, a furniture article, a garment, and combinations thereof.

4. The method of claim 1, wherein the substrate comprises a material selected from the group consisting of a metal, a metal alloy, a polymer, a membrane, a textile, and combinations thereof.

5. The method of claim 1, wherein the substrate comprises stainless steel.

6. The method of claim 1, wherein the nucleating agent is selected from the group consisting of sodium borohydride, hydrazine, D-glucose, hyaluronic acid, and combinations thereof.

7. The method of claim 1, wherein the nucleating agent is D-glucose.

8. The method of claim 1, wherein the nucleating agent has a concentration from about 3 mM to about 300 mM.

9. The method of claim 1, wherein the sulfidation agent is selected from the group consisting of sodium sulfide, sodium thiosulfate, thiocarbamide, thioacetamide, and combinations thereof.

10. The method of claim 1, wherein the sulfidation agent is sodium sulfide.

11. The method of claim 1, wherein the sulfidation agent has a concentration from about $10^{-1}$ M to about $10^{-5}$ M.

12. The method of claim 1, wherein applying the sulfidation agent to the silver cores is done for a time period of from about 1 hour to about 12 hours.

13. The method of claim 1, wherein the silver cores have a diameter from about 10 nm to about 100 nm.

14. A coating formed by the method of claim 1.

15. A composition comprising a plurality of sulfidated silver nanoparticles having a core-shell structure.

16. A substrate having a surface coated with the composition of claim 15.

17. The substrate of claim 16, wherein the plurality of sulfidated silver nanoparticles are uniformly distributed on the surface.

18. The substrate of claim 16, wherein the substrate is selected from the group consisting of a water treatment instrument, a surgical instrument, an implantable medical device, a catheter, a bandage, a furniture article, a garment, and combinations thereof.

19. The substrate of claim 16, wherein the substrate comprises a material selected from the group consisting of a metal, a metal alloy, a polymer, a membrane, a textile, and combinations thereof.

20. The substrate of claim 16, wherein the substrate comprises stainless steel.

* * * * *